(12) United States Patent
Xie et al.

(10) Patent No.: US 10,694,937 B2
(45) Date of Patent: Jun. 30, 2020

(54) HAND-HELD AUTONOMOUS VISUAL ACUITY MEASUREMENT APPARATUS AND VISUAL ACUITY MEASURING METHOD

(71) Applicant: SUZHOU SEEHITECH EQUIPMENTS CO., LTD, Suzhou, Jiangsu (CN)

(72) Inventors: Pei Xie, Jiangsu (CN); Qin Jiang, Jiangsu (CN); Renyuan Chu, Jiangsu (CN); Xingtao Zhou, Jiangsu (CN); Qinmei Wang, Jiangsu (CN); Junwen Zeng, Jiangsu (CN); Ruihua Wei, Jiangsu (CN); Ji Shen, Jiangsu (CN)

(73) Assignee: SUZHOU SEEHITECH EQUIPMENTS CO., LTD., Suzhou, Jiangsu (CN)

( * ) Notice: Subject to any disclaimer, the term of this patent is extended or adjusted under 35 U.S.C. 154(b) by 262 days.

(21) Appl. No.: 15/737,562

(22) PCT Filed: Aug. 16, 2016

(86) PCT No.: PCT/CN2016/095558
§ 371 (c)(1),
(2) Date: Dec. 18, 2017

(87) PCT Pub. No.: WO2016/202311
PCT Pub. Date: Dec. 22, 2016

(65) Prior Publication Data
US 2018/0177392 A1    Jun. 28, 2018

(30) Foreign Application Priority Data

Jun. 18, 2015    (CN) .......................... 2015 1 0340549

(51) Int. Cl.
*A61B 3/028*    (2006.01)
*A61B 3/103*    (2006.01)
(Continued)

(52) U.S. Cl.
CPC ............. *A61B 3/028* (2013.01); *A61B 3/0091* (2013.01); *A61B 3/103* (2013.01); *A61B 3/107* (2013.01); *A61B 3/14* (2013.01)

(58) Field of Classification Search
CPC ........... A61B 3/14; A61B 3/0025; A61B 3/12; A61B 3/102; A61B 3/0008; A61B 3/0058;
(Continued)

(56) References Cited

U.S. PATENT DOCUMENTS 5,500,697 A    3/1996 Fujieda
2015/0374232 A1*    12/2015 Yoshino .................. A61B 3/12
351/206
(Continued)

FOREIGN PATENT DOCUMENTS

CN    102525402    7/2012
CN    102715886    10/2012
(Continued)

OTHER PUBLICATIONS

Written Opinion of the International Search Authority (ISA/237) for PCT/CN2016/095558—Chinese Patent Office; dated May 1, 2017.
(Continued)

*Primary Examiner* — Thomas K Pham
*Assistant Examiner* — Sharrief I Broome
(74) *Attorney, Agent, or Firm* — Baker, Donelson, Bearman, Caldwell & Berkowitz, PC

(57) ABSTRACT

The present invention discloses a hand-held autonomous visual acuity measurement apparatus and a visual acuity measuring method. The invention comprises a corneal curvature measurement module comprising a first light source for emitting a first light beam and a first image collector for collecting an image formed from the first light beam after it has been reflected by cornea, the first image collector being
(Continued)

movably provided in the corneal curvature measurement optical path of the corneal curvature measurement module, and the corneal curvature measurement module further comprises a first motor for driving the first image collector to move along the corneal curvature measurement optical path so that the first image collector moves to the imaging position. Employing the first motor to drive the first image collector to automatically focus, requires no assistance from a second person to adjust the focus, and the subject may complete the vision measurement by oneself, the present invention has capability of being operated by one subject, and convenient visual acuity measurement, and can effectively achieve miniaturization and portability of optometry systems.

10 Claims, 2 Drawing Sheets

(51) Int. Cl.
*A61B 3/107* (2006.01)
*A61B 3/14* (2006.01)
*A61B 3/00* (2006.01)

(58) Field of Classification Search
CPC ..... A61B 3/1225; A61B 3/1025; A61B 3/113; A61B 3/145; A61B 3/0091; A61B 3/0041; A61B 3/117; A61B 3/103; A61B 3/1005; A61B 3/1015; A61B 3/112; A61B 3/13; A61B 3/0033; A61B 3/107; G01B 9/02091; G01B 9/02044; G01B 9/02004; G01B 9/02027; G01B 2290/45; G01B 2290/70; G01B 9/0203; G01B 9/02083; G01B 2290/65; G01B 9/02041; G01B 9/02087; G01B 11/2518; G01B 9/0201; G01B 9/02011; G01B 9/02028; G01B 9/02034; G01B 9/02039; G01B 9/02045; G01B 9/02048; G01B 9/0205; G06T 2207/30041; G06T 2207/10101; G06T 7/0012; G06T 2207/20056; G06T 5/50; G06T 7/248; G06T 15/00; G06T 15/04; G06T 2207/10028; G06T 2207/10048; G06T 2207/10144; G06T 2207/20081; G06T 2207/30096; G06T 2207/30101; G06T 2207/30104; G06T 3/0018; G06T 3/0062; G06T 3/4053; G06T 5/005; G06T 7/0014; G02B 27/141; G02B 26/101; G02B 27/0068; G02B 26/0833; G02B 27/1013; G02B 7/023; G02B 7/04; G02B 13/0095; G02B 17/006; G02B 17/08; G02B 17/0832; G02B 2027/0185; G02B 2027/0187; G02B 21/0048; G02B 21/0056; G02B 21/025; G02B 21/22; G02B 21/362; G02B 21/367; G02B 26/023

See application file for complete search history.

(56) References Cited

U.S. PATENT DOCUMENTS

2018/0125361 A1* 5/2018 Okuda ................. A61B 3/102
2018/0353067 A1* 12/2018 Moriguchi ........... A61B 3/1225

FOREIGN PATENT DOCUMENTS

| CN | 103340596 | 10/2013 |
|----|-----------|---------|
| CN | 103767675 | 5/2014 |
| CN | 104095610 | 10/2014 |
| CN | 104398236 | 3/2015 |
| CN | 104887176 | 9/2015 |
| CN | 204744101 | 11/2015 |
| CN | 101732030 | 6/2016 |
| JP | 06-311965 | 8/1994 |
| JP | 2002360516 | 12/2002 |

OTHER PUBLICATIONS

International Search Report (ISA/210) for PCT/CN2016/095558; dated May 1, 2017.
First Office Action from Chinese Patent Office for Application 201510340549.X, dated Feb. 24, 2016; Reference No. 2016021901182140.
Second Office Action from Chinese Patent Office for Application 201510340549.X, dated Nov. 4, 2016; Reference No. 2016110101690120.

* cited by examiner

HAND-HELD AUTONOMOUS VISUAL ACUITY MEASUREMENT APPARATUS AND VISUAL ACUITY MEASURING METHOD

CROSS REFERENCE TO RELATED APPLICATIONS

This application is a § 371 National Stage Application of PCT/CN2016/095558 filed Aug. 16, 2016, which claims priority to CN201510340549.X filed Jun. 18, 2015, which are hereby incorporated by reference in their entirety.

TECHNICAL FIELD OF THE INVENTION

The present invention relates to a hand-held autonomous visual acuity measurement apparatus and a visual acuity measuring method.

BACKGROUND OF THE INVENTION

At present, the traditional optometry instruments have a large volume, and are not portable. And, it requires the user have certain professional knowledge, or it needs the professional optometrist to measure the visual acuity of the subject, and the subject cannot independently complete the visual acuity measurement. The working principle of traditional optometry instrument is: the subject fixes the fixed optotype inside (or outside) the instrument, and the measurement crew operates the three-dimensional joystick of the optometer, adjusts the three-dimensional distance between the optometer and the human eye to make the human eye in the working position of the optometry system, and then measures the visual acuity, the chin and forehead of the subject must be close to the measuring bracket tightly during operation. For those who do not cooperate with the measurement, or the measurer does not have enough professional skills, it results in inaccurate actual measurement results, which directly affect the accuracy of vision correction when configuring glasses.

SUMMARY OF THE INVENTION

Aiming at the above mentioned problems, the purpose of the present invention is to provide a hand-held autonomous visual acuity measurement apparatus and a visual acuity measuring method.

To achieve the above aims, a technical scheme employed by the present disclosure is:

A hand-held autonomous visual acuity measurement apparatus, comprising a corneal curvature measurement module, and the corneal curvature measurement module comprises a first light source for emitting a first light beam and a first image collector for collecting an image formed from the first light beam after it has been reflected by cornea, the first image collector is movably provided in the corneal curvature measurement optical path of the corneal curvature measurement module, and the corneal curvature measurement module further comprises a first motor for driving the first image collector to move along the corneal curvature measurement optical path so that the first image collector moves to the imaging position.

Preferably, the first light source comprises a plurality of LED projection module groups, and the plurality of LED projection module groups is annularly arranged at equal intervals.

Preferably, the visual acuity measurement apparatus further comprises a fixation vision module and a first dichroic mirror, and the first dichroic mirror totally transmits visible light and totally reflects the first light beam for the user to gaze at the fixation vision module through the first dichroic mirror during the measurement, and the first dichroic mirror is disposed in the emergent light path of the first light source.

More preferably, the fixation vision module comprises a first lens group as well as a second lens group disposed between the first lens group and the first dichroic mirror.

More preferably, the visual acuity measurement apparatus further comprises a diopter measurement module comprising a second light source for emitting a second light beam and a second image collector for collecting an image formed from the second light beam after it has been reflected by cornea, and the first dichroic mirror enables total transmission of visible light and total reflection of the first light beam and the second light beam, and the first dichroic mirror is disposed in the emergent light paths of the first light source and the second light source.

Further, the second image collector is movably provided in the diopter measurement optical path of the diopter measurement module, and the diopter measurement module further comprises a second motor for driving the second image collector to move along the diopter measurement optical path so that the second image collector moves to the imaging position.

Further, the visual acuity measurement apparatus further comprises a second dichroic mirror totally reflecting the first light beam and totally transmitting the second light beam, the first dichroic mirror and the second dichroic mirror are respectively disposed in the corneal curvature measurement optical path and the diopter measurement optical path, and the visual acuity measurement apparatus further comprises a beam splitter with an oval reflective surface, the beam splitter is disposed in the diopter measurement optical path and located behind the second dichroic mirror.

Preferably, the wave length of the first light beam is 900-1000 nm, and the wave length of the second light beam is 790-870 nm, and both of the first image collector and the second image collector are photoelectric detectors.

Preferably, the visual acuity measurement apparatus further comprises a data storage module for storing diopter and corneal curvature data and a transmission module for transmitting the diopter and corneal curvature data to a cloud server.

Another technical scheme employed by the present disclosure is:

A visual acuity measuring method, comprises the following steps:

S1 corneal curvature measurement: an incidence angle of a first light beam incident on the cornea is θ, a curvature radius of the cornea is $R_1$, obtaining the pixel of a circle center of a collected image according to the collected image, fitting the obtained circle center into a circle and obtaining a radius $R_2$ of the fitting circle, the total magnification factor of a third lens group and a fourth lens group is $\beta_1$, and the corneal curvature radius is expressed by formula (1), $$R_1 = \frac{2R_2}{\beta_1 \times \tan\theta} \tag{1}$$

formula (1) is expressed as formula (2) by polynomial fitting, $$R_1 = a_0 + a_1 \times R_2 + a_2 \times R_2^2 + a_3 \times R_2^3 \tag{2}$$

calibrating a visual acuity measurement apparatus with a plurality of standard model eyes, corneal curvatures of respective standard model eyes are known and different from each other, and obtaining the values of $a_0$, $a_1$, $a_2$ and a; according to the collected image reflected by a subject's cornea, obtaining the curvature radius $R_2$ of the corresponding fitting circle, and according to formula (2), obtaining the corneal curvature radius $R_1$ of the subject;

S2 diopter measurement comprises:

S201 diopter measurement calibration: the relationship between the diopter and the respective lens groups in the imaging optical path are expressed by formulas (3), (4) and (5):

$$\frac{1}{l'_3} - \frac{1}{-\frac{1}{D_0} - L_0} = \frac{1}{f'_3} \quad (3)$$

$$\frac{1}{l'_5} - \frac{1}{l'_3 - \Delta l_{35}} = \frac{1}{f'_5} \quad (4)$$

$$\frac{1}{l'_6} - \frac{1}{l'_5 - \Delta l_{56}} = \frac{1}{f'_6} \quad (5)$$

wherein, $L_0$ is a distance from the third lens group to the cornea, $D_0$ is diopter of a human eye in a standard position, $f'_3$, $f'_5$ and $f'_6$ are respectively focal lengths of the third lens group, a fifth lens group and a sixth lens group, $l'_3$, $l'_5$, and $l'_6$ are respectively image distances of images of a light spot on the retina after imaging through the third lens group, the fifth lens group and the sixth lens group, $\Delta l_{35}$ is the space between the third lens group and the fifth lens group, $\Delta l_{56}$ is the space between the fifth lens group and the sixth lens group, obtaining a fourth-order polynomial by fitting formulas (3), (4) and (5), calibrating the visual acuity measurement apparatus with a plurality of standard model eyes, and diopters of respective standard model eyes are known and different from each other, obtaining the values of respective coefficients of the above fourth-order polynomial; during the measurement, measuring an image distance $l'_6$ of the sixth lens group, and then obtaining the diopter $D_0$ of a human eye in the standard position according to the above fourth-order polynomial;

S202 diopter compensation: calibrating the visual acuity measurement apparatus using a standard model eye with a known corneal curvature, moving the standard model eye and detecting imaging positions of a first light beam when the standard eye is located at different positions, and obtaining a correspondence between the position of the cornea and the imaging position of the first light beam; measuring the corneal curvature of a subject and obtaining an actual imaging position of the first light beam, obtaining a current position of the subject's cornea according to the correspondence between the position of the cornea and the imaging position of the first light beam, and comparing the distance from the third lens group to the current position of the cornea with $L_0$ to obtain a displacement difference $\Delta x$; compensating the diopter $D_0$, and the compensated diopter is the actual diopter D of the subject, the relationship between the actual diopter D and the diopter $D_0$ of the human eye in the standard position is shown in formula (6).

$$D = \frac{1}{\frac{1}{D_0} - \Delta x} \quad (6)$$

The above mentioned technical scheme employed by the present disclosure has the following advantages over the prior art: the present disclosure employs the motor to drive the first image collector to automatically focus, requires no assistance from a second person to adjust the focus, and the subject may complete the vision measurement by oneself, the present invention has capability of being operated by one subject, and convenient visual acuity measurement, and can effectively achieve miniaturization and portability of optometry systems.

Wherein, 1—first lens group; 2—second lens group; 3—first dichroic mirror; 4—first light source; 5—third lens group; 6—second dichroic mirror; 7—fourth lens group; 8—first image collector; 9—second light source; 10—diaphragm; 11—seventh lens group; 12—beam splitter; 13—fifth lens group; 14—sixth lens group; 15—second image collector.

DETAILED DESCRIPTION OF EXEMPLARY EMBODIMENTS

In the following, the preferable embodiments of the present disclosure are explained in detail combining with the accompanying drawings so that the advantages and features of the present disclosure can be easily understood by the skilled persons in the art.

Figure 1:
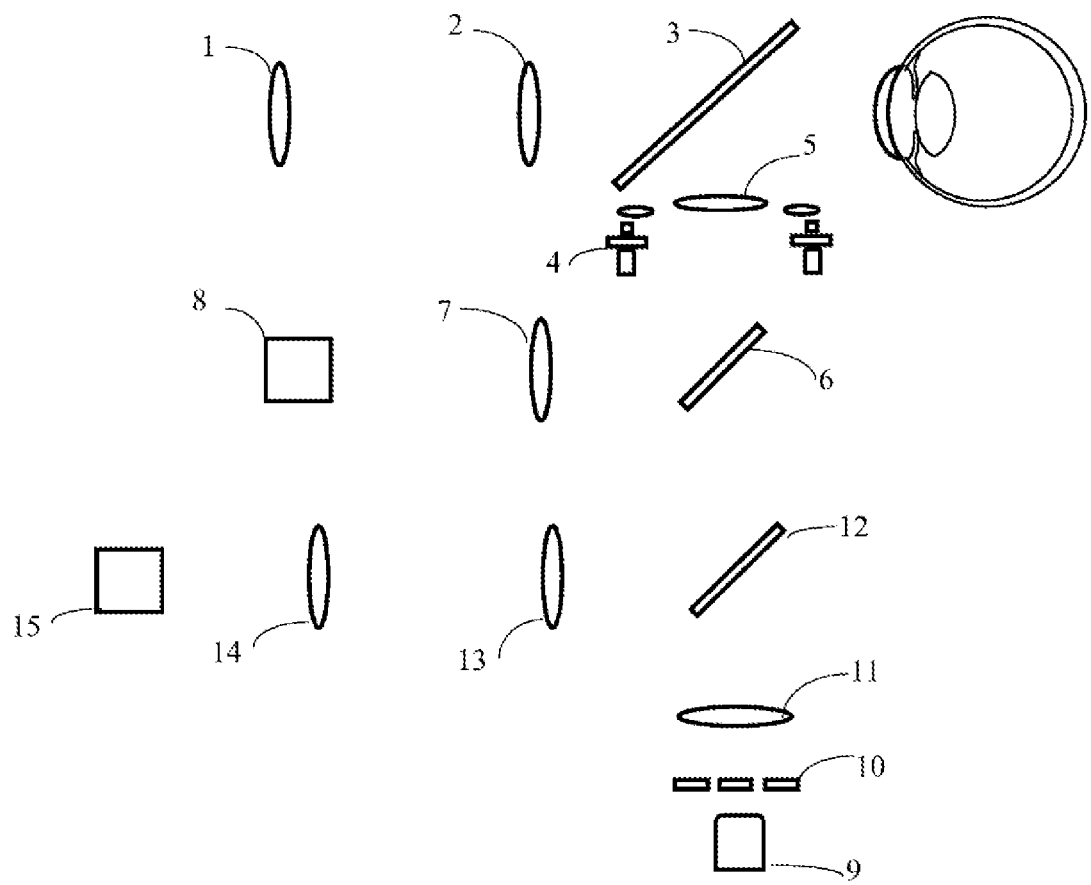
FIG. 1 is a schematic structure diagram of the visual acuity measurement apparatus of the present disclosure.

FIG. 1 shows a hand-held autonomous visual acuity measurement apparatus of the present invention. Combining with FIG. 1, the visual acuity measurement apparatus comprises a first lens group 1, a second lens group 2, a first dichroic mirror 3, a first light source 4, a third lens group 5, a second dichroic mirror 6, a fourth lens group 7, a first image collector 8, a first motor (not shown in the figure), a second light source 9, a diaphragm 10, a seventh lens group 11, a beam splitter 12, a fifth lens group 13, a sixth lens group 14, a second image collector 15 and a second motor (not shown in the figure).

The first lens group 1 and the second lens group 2 form a fixation vision module for a human eye to gaze at, and the fixation vision module employ a telescopic system and controls the viewing direction and the viewing point of the human eye, and the exit pupil of the fixation vision module is consistent with human eye pupil. The first light source 4, the first dichroic mirror 3, the third lens group 5, the second dichroic mirror 6, the fourth lens group 7, the first image collector 8 and the first motor form a corneal curvature measurement module for measuring the corneal curvature. The second light source 9, the diaphragm 10, the seventh lens group 11, the beam splitter 12, the second dichroic mirror 6, the third lens group 5, the first dichroic mirror 3, the fifth lens group 13, the sixth lens group 14, the second image collector 15 and the second motor form a diopter measurement module for measuring the diopter.

Figure 2:
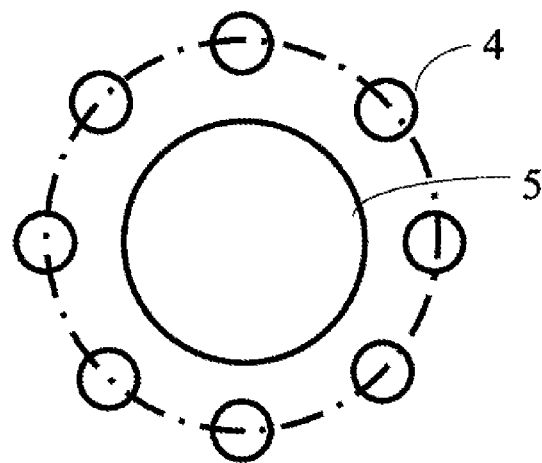
FIG. 2 is a schematic arrangement diagram of the first light source and the third lens group of the present disclosure.

The emergency light paths of the light sources of the corneal curvature measurement module and the diopter measurement module are as follows:

The first light source 4 emits a first light beam in infrared band with a wave length of 900-1000 nm. Combining with FIG. 2, the first light source 4 comprises eight LED projection module groups, and the eight LED projection module groups are annularly arranged around the center axis of the third lens group 5 at equal intervals. Each LED projection module consists of a LED light, a diffuser, a light hole and the first light source 4. The emitted first light beam is an annular infrared light. The first dichroic mirror 3 totally transmits visible light and totally reflects the first light beam. The first dichroic mirror 3 is disposed in the emergency light path of the first light source 4 for reflecting the first light beam to the human eye, and the second lens group 2 is disposed between the first lens group 1 and the first dichroic mirror 3, the human eye gazes at the second lens group 2 and the first lens group 1 through the first dichroic mirror 3, keeping in a relaxed state.

Figure 3:
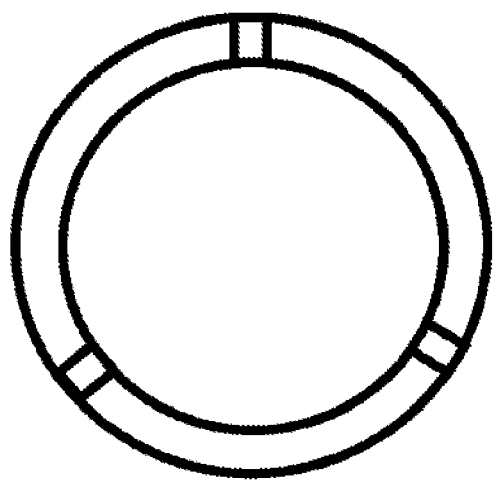
FIG. 3 is a schematic diagram of the annular diaphragm of the present disclosure.

The second light source 9 emits a second light beam in near-infrared band with a wave length of 790-870 nm. The diaphragm 10, the seventh lens group 11, the beam splitter 12, the second dichroic mirror 6, the third lens group 5, the first dichroic mirror 3 are disposed in the emergency light path of the second light source 9 successively. Combining with FIG. 3, the diaphragm 10 is an annular diaphragm 10, and the second light beam passing through the annular diaphragm 10 is an annular near-infrared light. The second dichroic mirror 6 totally transmits the second light beam (a near-infrared light with a wave length of 790-870 nm) and totally reflects the first light beam (an infrared light with a wave length of 900-1000 nm). The first dichroic mirror 3 totally reflects near-infrared light (the near-infrared light with a wave length of 790-870 nm) and infrared light (the infrared light with a wave length of 900-1000 nm), and totally transmits visible light (a light with a wave length of 400-700 nm). The second beam transmits through the beam splitter 12, the seventh lens group 11 and the second dichroic mirror 6 successively, is converged via the third lens group 5, and then is reflected by the first dichroic mirror 3 to the retina.

The image collecting processes of the corneal curvature measurement module and the diopter measurement module are as follows:

The first dichroic mirror 3, the third lens group 5, the second dichroic mirror 6, the fourth lens group 7, the first image collector 8 are disposed in the imaging light path of the first light beam successively. The first light beam reflected by the cornea is again reflected by the first dichroic mirror 3 to change the propagation direction, converged via the third lens group 5 and reflected by the second dichroic mirror 6 to change the propagation direction again, then converged via the fourth lens group 7 to image, and the first motor drives the first image collector 8 to automatically focus and moves the first image collector 8 to the imaging position to collect the image.

Figure 4A:
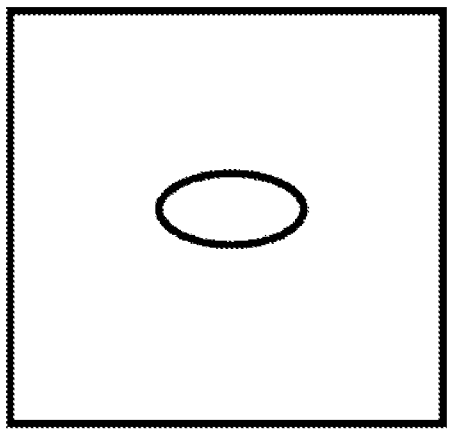
FIGS. 4a and 4b are a front view and a schematic projection diagram along the diopter measurement light path of the beam splitter of the present disclosure.
Figure 4B:
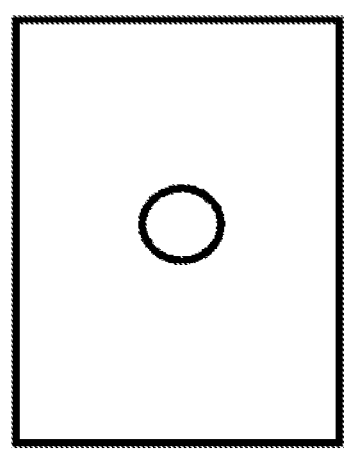

The first dichroic mirror 3, the third lens group 5, the second dichroic mirror 6, the beam splitter 12, the fifth lens group 13, the sixth lens group 14 and the second image collector 15 are disposed in the imaging light path of the second light beam successively. Combining with FIGS. 4a and 4b, the beam splitter 12 comprises a reflective surface formed in the middle of the beam splitter 12, the reflective surface presents an oval shape, and the orthographic projection of the reflective surface along the imaging light path of the second light beam is a circle. The second light beam reflected by the cornea is again reflected by the first dichroic mirror 3 to change the propagation direction, converged via the third lens group 5, transmitted through the second dichroic mirror 6 and reflected by the reflective surface of the beam splitter 12 to change the propagation direction, and then converged via the fifth lens group 13 and imaged via the sixth lens group 14, and the second motor drives the second image collector 15 to automatically focus and moves the second image collector 15 to the imaging position to collect the image.

The visual acuity measurement apparatus further comprises a data storage module and a wireless transmission module. The data storage module is used for storing the data of the diopter and the corneal curvature. The wireless transmission module is used for transmitting the data of the diopter and the corneal curvature to a cloud server, for a long time storage facilitating follow-up checking and for doctors to analyze.

In the present embodiment, both of the first image collector 8 and the second image collector 15 are photoelectric detectors.

The visual acuity measuring method of the present disclosure comprises S1 corneal curvature measurement and S2 diopter measurement.

S1 corneal curvature measurement: an incidence angle of a first light beam incident on the cornea is $\theta$, a curvature radius of the cornea is $R_1$, obtaining the pixel of a circle center of a collected annular image according to the annular image collected by the first image collector 8, fitting the obtained circle center into a circle and obtaining a radius $R_2$ of the fitting circle, a total magnification factor of the third lens group 5 and the fourth lens group 7 is $\beta_1$, and the corneal curvature radius is expressed by formula (1), $$R_1 = \frac{2R_2}{\beta_1 \times \tan\theta} \tag{1}$$

formula (1) is expressed as formula (2) by polynomial fitting, $$R_1 = a_0 + a_1 \times R_2 + a_2 \times R_2^2 + a_3 \times R_2^3 \tag{2}$$

calibrating a visual acuity measurement apparatus with a plurality of (for example, ten) standard model eyes with known and different corneal curvatures, and obtaining the values of $a_0$, $a_1$, $a_2$ and $a_3$ according to the annular image reflected by a subject's cornea collected by the first image collector 8, obtaining the curvature radius $R_2$ of the corresponding fitting circle, and according to formula (2), obtaining the corneal curvature radius $R_1$ of the subject;

S2 diopter measurement comprises the following steps: S201 diopter measurement calibration, and S202 diopter compensation.

Figure 5:
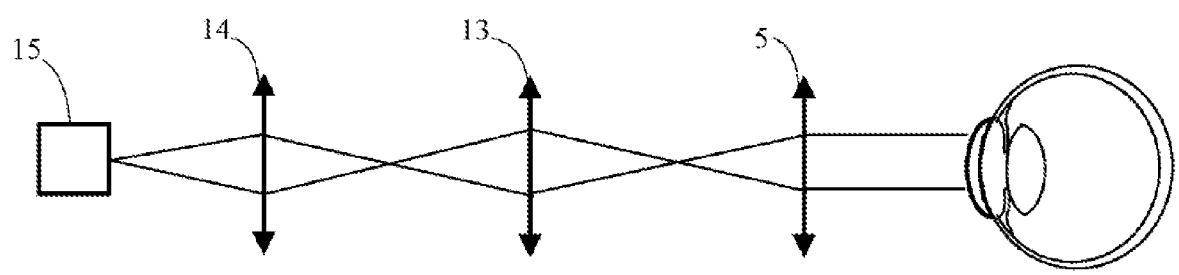
FIG. 5 is a schematic relationship diagram of the diopter and the respective lens groups in the imaging optical path thereof.

S201 diopter measurement calibration: combining with FIG. 5, the relationship between the diopter and the respective lens groups in the imaging optical path are expressed by formulas (3), (4) and (5):

$$\frac{1}{l'_3} - \frac{1}{-\frac{1}{D_0} - L_0} = \frac{1}{f'_3} \tag{3}$$

-continued $$\frac{1}{l'_5} - \frac{1}{l'_3 - \Delta l_{35}} = \frac{1}{f'_5} \quad (4)$$

$$\frac{1}{l'_6} - \frac{1}{l'_5 - \Delta l_{56}} = \frac{1}{f'_6} \quad (5)$$

wherein, $L_0$ is a distance from the third lens group 5 to the cornea, $D_0$ is diopter of a human eye in a standard position (the standard position is the reference position of the measurement), $f'_3$, $f'_5$ and $f'_6$ are respectively focal lengths of the third lens group 5, a fifth lens group 13 and a sixth lens group 14, $l'_3$, $l'_5$ and $l'_6$ are respectively image distances of images of a light spot on the retina after imaging through the third lens group 5, the fifth lens group 13 and the sixth lens group 14, $\Delta l_{35}$ is a space between the third lens group 5 and the fifth lens group 13, and $\Delta l_{56}$ is a space between the fifth lens group 13 and the sixth lens group 14;

obtaining a fourth-order polynomial by fitting formulas (3), (4) and (5), calibrating the visual acuity measurement apparatus with a plurality of standard model eyes, and diopters of respective standard model eyes are known and different from each other, and the diopter range of the standard model eyes is −20 D to 20 D, obtaining the values of respective coefficients of the above fourth-order polynomial;

during the measurement, selecting one point on a screw as a detecting point, and when the second motor drives the second image collector 15 via the screw and the like to move to the imaging position (where the image quality of the collected image is clearest), recording the position of the detecting point (or the rotation angle of the motor output shaft, the distance that the second image collector 15 moves), and then obtaining an image distance 16 of the sixth lens group 14, and then obtaining a diopter $D_0$ of the human eye in the standard position according to the above fourth-order polynomial;

S202 diopter compensation: when a front and rear deviation of the human eye occurs during measurement, the image positions will change, the present disclosure calibrates the visual acuity measurement apparatus using a standard model eye with a known corneal curvature, moves the standard model eye and detects imaging positions of the first light beam when the standard eye is located at different positions, and obtains a correspondence between the position of the cornea and the imaging position of the first light beam; measures a corneal curvature of the subject and obtains an actual imaging position of the first light beam, obtains a current position of the subject's cornea according to the correspondence between the position of the cornea and the imaging position of the first light beam, and compares the distance from the current position of the cornea to the third lens group with $L_0$ to obtain a displacement difference $\Delta x$; compensates the diopter $D_0$, and the compensated diopter is the actual diopter D of the subject, the relationship between the actual diopter D and the diopter $D_0$ of the human eye in the standard position is shown in formula (6).

$$D = \frac{1}{\frac{1}{D_0} - \Delta x} \quad (6)$$

The technical scheme of the present disclosure has the following advantages over the prior art:

i. The corneal curvature measurement module and the diopter measurement module of the present disclosure employ respectively the first motor and the second motor to drive the first image collector 8 and the second image collector 15 to automatically focus, requires no assistance from a second person to adjust the focus, and the subject may complete the vision measurement by oneself, the present disclosure has capability of being operated by one subject, and convenient visual acuity measurement, and can effectively achieve miniaturization and portability of optometry systems.

ii. The present disclosure employs the first dichroic mirror 3 which totally transmits visible band (400-700 nm) and totally reflects infrared band (780-1000 nm), and when compared to the traditional optometry system, it can effectively prevent stimulation on the human eye from the first light source 4, and eliminate the influence of the human eye adjustment on the diopter measurement, and meanwhile, the high transmittance of the fixation vision module for the visible light region can also relax the human eye so as to be correctly observed.

iii. The present disclosure employs a telescopic system consisted of the first lens group 1 and the second lens group 2, the exit pupil of the fixation vision module is consistent with human eye pupil, and the field of view is only several degrees, and when compared with the fixation system of existing optometry instrument, it can effectively position the human eye in an correct observation position and let it in the relaxed state to observe objects in a correct angle.

iv. The present disclosure comprises a wireless transmission module which can upload the final visual acuity data in the measurement apparatus to a cloud server, the traditional visual acuity measuring system usually carries out the visual acuity measurement to the subject in a discrete and irregular manner, and the present disclosure can effectively collect the visual acuity data of the subject at different times, to facilitate conducting big data modeling of the subject's eyesight and analyzing the future development trend of the eyesight, to track and predict the eyesight of the subject.

The embodiments described above are only for illustrating the technical concepts and features of the present invention, are preferred embodiments, are intended to make those skilled in the art being able to understand the present invention and thereby implement it, and should not be concluded to limit the protective scope of this invention. Any equivalent variations or modifications according to the spirit of the present invention should be covered by the protective scope of the present invention.

The invention claimed is:

1. A hand-held autonomous visual acuity measurement apparatus, comprising a corneal curvature measurement module, wherein the corneal curvature measurement module comprises a first light source for emitting a first light beam and a first image collector for collecting an image formed from the first light beam after the first light beam has been reflected by a cornea, the first image collector being movably provided in a corneal curvature measurement optical path of the corneal curvature measurement module, and the corneal curvature measurement module further comprises a first motor for driving the first image collector to move along the corneal curvature measurement optical path so that the first image collector moves to an imaging position, the visual acuity measurement apparatus further comprising a fixation vision module and a first dichroic mirror, and the first dichroic mirror totally transmits visible light and totally reflects the first light beam for the user to gaze at the fixation vision module through the first dichroic mirror during the measurement, and the first dichroic mirror is disposed in an emergent light path of the first light source;

the visual acuity measurement apparatus further comprising a diopter measurement module comprising a second light source for emitting a second light beam and a second image collector for collecting an image formed from the second light beam after it has been reflected by the cornea, and the first dichroic mirror enables total transmission of visible light and total reflection of the first light beam and the second light beam, and the first dichroic mirror is disposed in the emergent light paths of the first light source and the second light source.

2. The visual acuity measurement apparatus according to claim 1, wherein the first light source comprises a plurality of LED projection module groups, and the plurality of LED projection module groups is annularly arranged at equal intervals.

3. The visual acuity measurement apparatus according to claim 1, wherein the fixation vision module comprises a first lens group as well as a second lens group disposed between the first lens group and the first dichroic mirror.

4. The visual acuity measurement apparatus according to claim 1, wherein the second image collector is movably provided in diopter measurement optical path of the diopter measurement module, and the diopter measurement module further comprises a second motor for driving the second image collector to move along the diopter measurement optical path so that the second image collector moves to the imaging position.

5. The visual acuity measurement apparatus according to claim 1, wherein the visual acuity measurement apparatus further comprises a second dichroic mirror totally reflecting the first light beam and totally transmitting the second light beam, and the visual acuity measurement apparatus further comprises a beam splitter with an oval reflective surface, the beam splitter being disposed in diopter measurement optical path and located between the second dichroic mirror and the second image collector.

6. The visual acuity measurement apparatus according to claim 1, wherein the visual acuity measurement apparatus comprises a first dichroic mirror, the first light source, a third lens group, a second dichroic mirror, a fourth lens group, the first image collector, the first motor, a second light source, a diaphragm, a seventh lens group, a beam splitter, a fifth lens group, a sixth lens group, a second image collector, and a second motor;

the first light source, the first dichroic mirror, the third lens group, the second dichroic mirror, the fourth lens group, the first image collector and the first motor form the corneal curvature measurement module;

the second light source, the diaphragm, the seventh lens group, the beam splitter, the second dichroic mirror, the third lens group, the first dichroic mirror, the fifth lens group, the sixth lens group, the second image collector and the second motor form a diopter measurement module, and the second image collector is driven by the second motor and movably provided in diopter measurement optical path of the diopter measurement module.

7. The visual acuity measurement apparatus according to 1, wherein the wave length of the first light beam is 900-1000 nm, and the wave length of the second light beam is 790-870 nm.

8. The visual acuity measurement apparatus according to claim 1, wherein both the first image collector and the second image collector are photoelectric detectors.

9. The visual acuity measurement apparatus according to claim 1, wherein the visual acuity measurement apparatus further comprises a data storage module for storing data of diopter and corneal curvature and a transmission module for transmitting the data of diopter and corneal curvature to a cloud server.

10. A visual acuity measuring method, comprising the following steps:

S1 corneal curvature measurement: an incidence angle of a first light beam incident on a cornea is $\theta$, a curvature radius of the cornea is $R_1$, obtaining a pixel of a circle center of a collected image according to the collected image, fitting the obtained circle center into a circle and obtaining a radius $R_2$ of the fitting circle, a total magnification factor of a third lens group and a fourth lens group is $\beta_1$, and the corneal curvature radius is expressed by formula (1), $$R_1 = \frac{2R_2}{\beta_1 \times \tan\theta} \quad (1)$$

formula (1) is expressed as formula (2) by polynomial fitting, $$R_1 = a_0 + a_1 \times R_2 + a_2 \times R_2^2 + a_3 \times R_2^3 \quad (2)$$

calibrating a visual acuity measurement apparatus with a plurality of standard model eyes, corneal curvatures of respective standard model eyes are known and different from each other, and obtaining the values of $a_0$, $a_1$, $a_2$ and $a_3$; according to the collected image reflected by a subject's cornea, obtaining the curvature radius $R_2$ of the corresponding fitting circle, and according to formula (2), obtaining the corneal curvature radius $R_1$ of the subject;

S2 diopter measurement comprises:

S201 diopter measurement calibration: the relationship between a diopter and the respective lens groups in an imaging optical path are expressed by formulas (3), (4) and (5):

$$\frac{1}{l_3'} - \frac{1}{-\frac{1}{D_0} - L_0} = \frac{1}{f_3'} \quad (3)$$

$$\frac{1}{l_5'} - \frac{1}{l_3' - \Delta l_{35}} = \frac{1}{f_5'} \quad (4)$$

$$\frac{1}{l_6'} - \frac{1}{l_5' - \Delta l_{56}} = \frac{1}{f_6'} \quad (5)$$

wherein, $L_0$ is a distance from the third lens group to the cornea, $D_0$ is the diopter of a human eye in a standard position, $f'_3$, $f'_5$ and $f'_6$ are respectively focal lengths of the third lens group, a fifth lens group and a sixth lens group, $l'_3$, $l'_5$ and $l'_6$ are respectively image distances of images of a light spot on the retina after imaging through the third lens group, the fifth lens group and the sixth lens group, $\Delta l_{35}$ is a space between the third lens group and the fifth lens group, $\Delta l_{56}$ is a space between the fifth lens group and the sixth lens group, obtaining a fourth-order polynomial by fitting formulas (3), (4) and (5), calibrating the visual acuity measurement apparatus with a plurality of standard model eyes, and the diopters of respective standard model eyes are known and different from each other, obtaining the values of respective coefficients of the above fourth-order polynomial; during the measurement, measuring an image distance $l'_6$ of the sixth lens group, and then obtaining the diopter $D_0$ of a human eye in the standard position according to the above fourth-order polynomial;

S202 diopter compensation: calibrating the visual acuity measurement apparatus using a standard model eye with a known corneal curvature, moving the standard model eye and detecting imaging positions of a first light beam when the standard eye is located at different positions, and obtaining a correspondence between the position of the cornea and the imaging position of the first light beam; measuring the corneal curvature of a subject and obtaining an actual imaging position of the first light beam, obtaining a current position of the subject's cornea according to the correspondence between the position of the cornea and the imaging position of the first light beam, and comparing the distance from the third lens group to the current position of the cornea with $L_0$ to obtain a displacement difference $\Delta x$; compensating the diopter $D_0$, and the compensated diopter is the actual diopter $D$ of the subject, the relationship between the actual diopter $D$ and the diopter $D_0$ of the human eye in the standard position is shown in formula (6):

$$D = \frac{1}{\frac{1}{D_0} - \Delta x}. \tag{6}$$

* * * * *